United States Patent [19]

Ishibashi

[11] Patent Number: 5,667,525
[45] Date of Patent: Sep. 16, 1997

[54] GRASPING FORCEPS FOR ENDOSCOPE

[75] Inventor: Yayoi Ishibashi, deceased, late of Yokohama, Japan, by Kenshi Ishibashi, Hitomi Kato Ishibashi, heirs

[73] Assignee: Olympus Optical Co., Tokyo, Japan

[21] Appl. No.: 504,785

[22] Filed: Jul. 20, 1995

[30] Foreign Application Priority Data

Aug. 25, 1994 [JP] Japan ................................. 6-200948

[51] Int. Cl.$^6$ ................................................. A61B 17/28
[52] U.S. Cl. .................................................. 606/206
[58] Field of Search ................................ 600/104, 139; 606/205-209; D24/143

[56] References Cited

U.S. PATENT DOCUMENTS

| | | | |
|---|---|---|---|
| 4,174,715 | 11/1979 | Hasson | 606/206 |
| 4,607,620 | 8/1986 | Storz | 606/206 X |
| 4,655,219 | 4/1987 | Petruzzi | 606/206 |
| 5,352,237 | 10/1994 | Rodak et al. | 606/205 X |
| 5,376,094 | 12/1994 | Kline | 606/205 X |
| 5,465,710 | 11/1995 | Miyagi et al. | 600/139 |

FOREIGN PATENT DOCUMENTS

| | | |
|---|---|---|
| 8535164 | 2/1986 | Germany . |
| 3626371 | 2/1987 | Germany . |
| 3709706 | 10/1987 | Germany . |

OTHER PUBLICATIONS

European Search Report dated Apr. 16, 1996, Ref. No.: 55 033 EP J/cl; Patent No. 95106352.8; Applicant: Olympus Optical Co., Ltd, listing above-cited references.

*Primary Examiner*—Richard J. Apley
*Assistant Examiner*—John P. Leubecker
*Attorney, Agent, or Firm*—Armstrong, Westerman, Hattori, McLeland & Naughton

[57] ABSTRACT

A grasping forceps for an endoscope including a flexible insertion section, an operating wire adapted to pass through the insertion section and to be advanced and retreated in accordance with the operating of an operating section connected with a hand-end side end portion thereof and at least four elastic grasping members of different lengths arranged at the leading end portion of the operating wire and having the habit of flexing such that leading end grasping portions formed at their leading end portions respectively spread outwardly from the central position of the insertion section. At least four elastic grasping members constructing the elastic grasping section are arranged in the order of increasing length to the leading end grasping portions with respect to the leading end face of the insertion section, and between the longest elastic grasping member and the shortest elastic grasping member in length to the leading end grasping portions in the circularly spread state of the elastic grasping members there are provided other elastic grasping members.

7 Claims, 7 Drawing Sheets

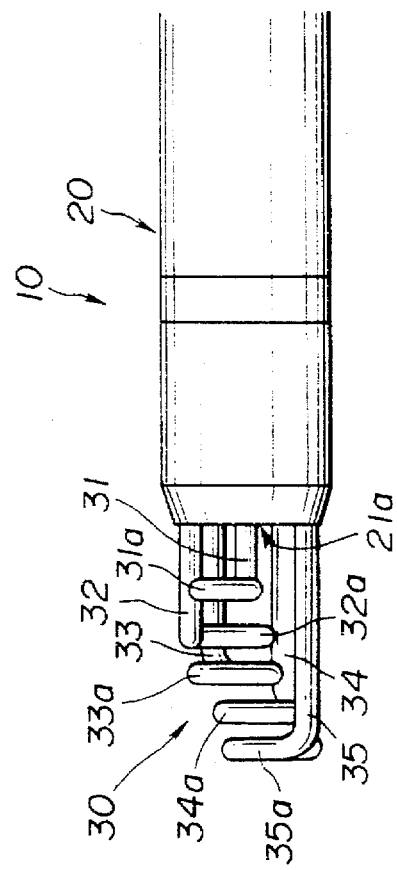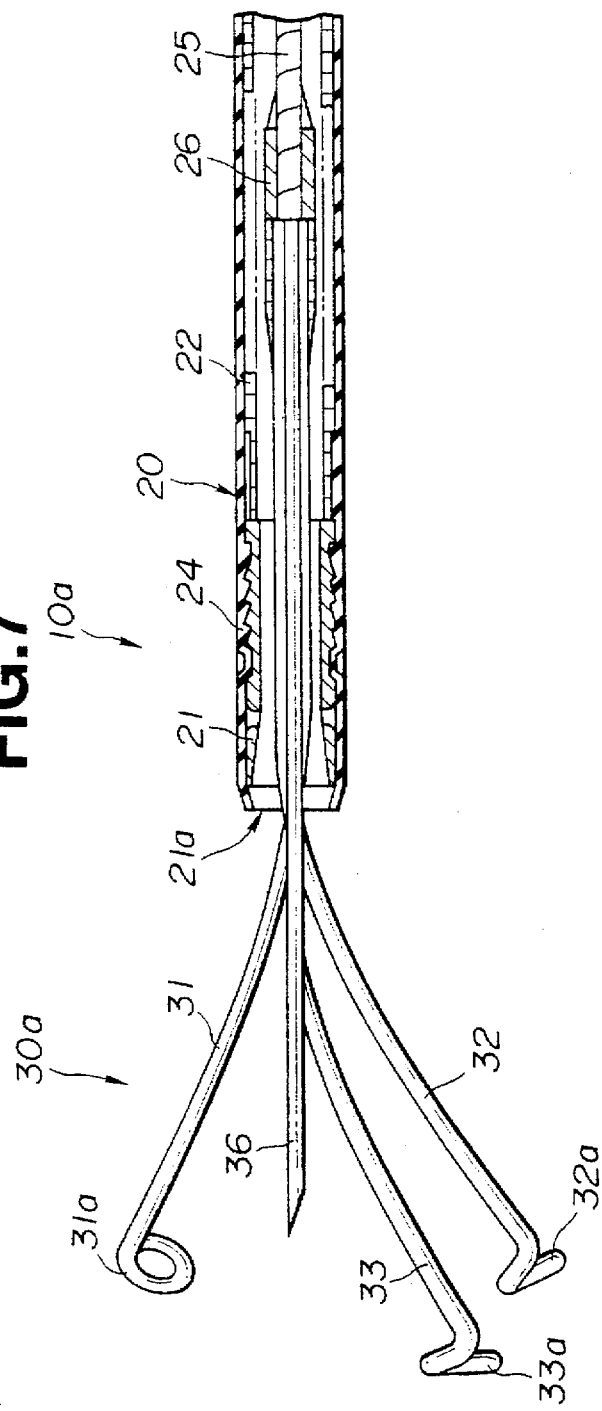

GRASPING FORCEPS FOR ENDOSCOPE

BACKGROUND OF THE INVENTION

1. Field of the Invention

The present invention relates to a grasping forceps insertable into a channel formed in an endoscope for allowing a treating instrument to pass therethrough. The forceps is used for grasping and picking out an object such as a foreign body, polypus and so on within a body cavity.

2. Description of the Related Art

Recently, in addition to the medical examination of a body cavity by an endoscope, there has been well-known in the art a grasping forceps for an endoscope such as an in vivo inspection forceps, where the grasping forceps is inserted into a treating instrument passing channel formed in the endoscope. The forceps is inserted into the body cavity for the purpose of grasping and recovering a foreign body within a living body or for grasping and picking out cellular tissue to be inspected.

The grasping forceps for the endoscope comprises a flexible insertion section composed of a coil sheath and the like externally covered with, for example, a flexible resin tube, an operation wire passing through this insertion section, an operating section connected with the operating wire at its hand-side end, and a grasping section composed of a plurality of elastic grasping members arranged at the leading end of the operating wire.

For example, as shown in FIG. 1, the elastic grasping section 2 of the grasping forceps 1 for the endoscope comprises three elastic grasping members 2a, 2b, 2c. This elastic grasping section 2 is connected at its hand-side end with the operating wire (not illustrated) passing through the interior of the insertion section 3, and the elastic grasping members 2a, 2b, 2c are projected and concealed from the leading end face 3a of the insertion section 3 in accordance with the advancing and retreating operations of the operating wire so as to open and close the elastic grasping section 2.

That is, when the operating wire is operationally pushed out, the elastic grasping members 2a, 2b, 2c are projected from the leading end face 3a of the insertion section 3. Thereupon, circular pawls 4a, 4b, 4c formed at the leading end portions of the respective elastic grasping members 2a, 2b, 2c are spread outward from the center of the insertion section 3 due to the elastic restoring forces of the elastic grasping members 2a, 2b, 2c. On one hand, as the elastic grasping members 2a, 2b, 2c are pulled into the insertion section 3 by the traction operation of the operating wire, the circular pawls 4a, 4b, 4c formed at the leading end portions of the elastic grasping members 2a, 2b, 2c are closed gradually to grasp a foreign body and the like.

But, since this forceps 1 for the endoscope has the elastic grasping section 2 composed of three grasping members 2a, 2b, 2c, the gaps between the adjacent elastic grasping members are wide. Therefore, the once grasped living body tissue or foreign body might occasionally drop through the gaps between the elastic grasping members.

Thereupon, in order to prevent the once grasped living body tissue or foreign body from dropping through the gaps between the elastic grasping members, the applicant of the present invention has proposed a forceps for an endoscope in Japanese Patent Application No. Hei. 6 (1994)-181503, wherein the elastic grasping section of the forceps for the endoscope comprises at least four elastic grasping members of different lengths, the circular pawls formed at the leading end portions of the elastic grasping members are arranged so as to come into a spiral fashion to narrow the gaps between the elastic grasping members when the elastic grasping members comprising those elastic grasping members of different lengths are spread, and the circular pawls formed at the leading end portions of the elastic grasping members can be converged within the insertion section in a longitudinally aligned manner.

In the forceps for the endoscope proposed in the above-mentioned Japanese Patent Application No. Hei. 6 (1994)-181503, however, when the elastic grasping portion composed of the elastic grasping members of different lengths is spread, since the elastic grasping section is constructed such that the circular pawls formed at the leading end portions of the elastic grasping members can be arranged in the spiral fashion, the longest elastic grasping member and the shortest grasping member are located at positions adjacent each other in the opened state.

As shown in FIG. 2, when the longest elastic grasping member 5e and the shortest elastic grasping member 5a of the elastic grasping members 5a, 5b, 5c, 5d, 5e having different lengths forming the elastic grasping section 5 are located at adjacent positions at random, the positional differential distance "a" between the circular grasping portion 6e of the longest elastic grasping member 5e and the circular grasping portion 6a of the shortest elastic grasping member 5a in the longitudinal direction of the insertion section becomes maximum in the opened state of the elastic grasping section 5, so that it is unlikely that they grasp a small polypus or foreign body.

SUMMARY OF THE INVENTION

It is an object of the present invention to provide a grasping forceps for an endoscope which is provided with an elastic grasping section which is capable of reliably grasping a small polypus or foreign body.

It is another object of the present invention to provide a treating instrument for an endoscope including a grasping forceps for an endoscope in which a leading end face of an insertion section to be inserted into a body cavity has increased safety.

In brief, a grasping forceps for an endoscope according to the present invention is provided with a flexible insertion section, an operating wire passing through the insertion section and connected at its proximal end with an operating section so as to be advanced and retreated in accordance with operation of the operating section, and at least four elastic grasping members of different lengths arranged at the leading end of the operating wire and having a flexing characteristic such that leading end grasping portions formed at their leading ends respectively tend to be spread from the center axis of the insertion section to the outside thereof, wherein at least four elastic grasping members forming the elastic grasping section are arranged in an order of increasing length to the leading end grasping portion with respect to the leading end face of the insertion section. Additional elastic grasping members are provided between the longest elastic grasping member and the shortest elastic grasping member to the leading end grasping portion in the circularly spread state of the elastic grasping members.

The other features and advantages of the present invention will become sufficiently apparent to those skilled in the art in view of the disclosure made in the following description thereof.

BRIEF DESCRIPTION OF THE DRAWINGS

FIG. 1 is an explanatory view showing the grasping forceps for the endoscope having the elastic grasping section composed of three elastic grasping members.

FIG. 2 is an explanatory view showing the grasping forceps for the endoscope having an elastic grasping section composed of five elastic grasping members of different lengths.

FIGS. 3 through 6 show a first embodiment of the present invention.

FIG. 3 is an explanatory view showing the grasping forceps for the endoscope of the present invention in use.

FIG. 4 is a sectional view explaining a construction of the grasping forceps for the endoscope of the present invention.

FIG. 5A is a perspective view showing the opened state of the elastic grasping section of the grasping forceps for the endoscope; and FIG. 5B is a longitudinal sectional view showing the opened state of the elastic grasping section of the grasping forceps for the endoscope.

FIG. 6 is a view showing a closed state of the elastic grasping section of the grasping forceps for the endoscope of the present invention.

FIG. 7 is a sectional view showing a schematic construction of a leading end portion of an insertion section of a grasping forceps for an endoscope according to the second embodiment of the present invention.

FIG. 10 is a sectional view showing a construction of a leading end portion of an insertion section of the high-frequency snare.

DETAILED DESCRIPTION OF THE PREFERRED EMBODIMENTS

A first embodiment of the present invention will be explained with reference to FIGS. 3 through 6.

Figure 1:
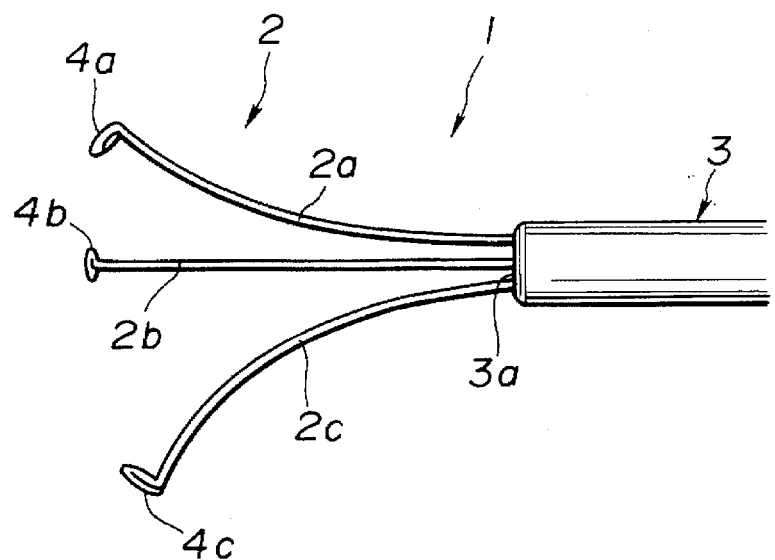
FIGS. 1 and 2 show a grasping portion of a conventional grasping forceps for an endoscope.
Figure 2:
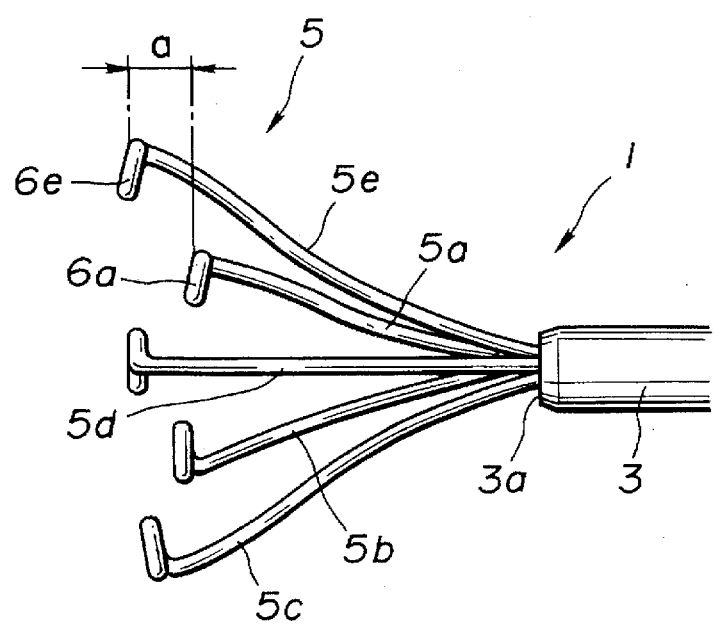
Figure 3:
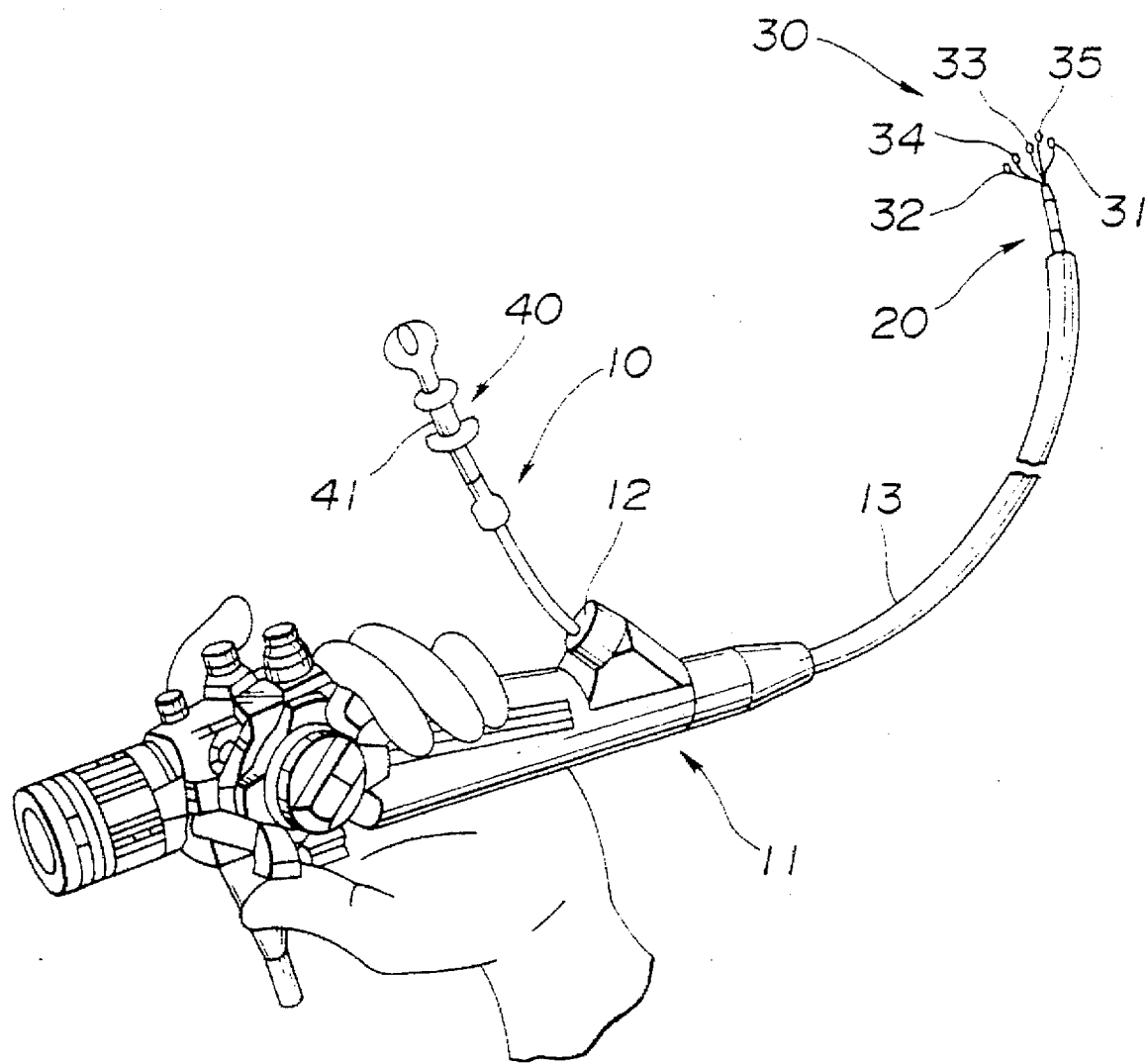

As shown in FIG. 3, a grasping forceps 10 for an endoscope is inserted from a treating instrument insertion opening 12 formed in the endoscope 11 into a forceps channel (not illustrated) formed within an endoscope insertion section 13 so as to pass through an insertion portion 20 for introduction into a body cavity. In this grasping forceps 10 for the endoscope, an elastic grasping section 30 composed of at least four elastic grasping members, for example, five elastic grasping members 31, 32, 33, 34, 35 in this embodiment, is disposed at the leading end portion of an operating wire passing through an internal bore of the insertion section 20 so as to be able to grasp and pick out an object such as a foreign body, polypus, living body tissue and so on within a body cavity. This elastic insertion section 30 is adapted to be opened and closed in accordance with pushing and pulling operations of a finger engagement portion 41 of an operating section 40 with which the operating wire is connected at its hand-side end.

Figure 4:
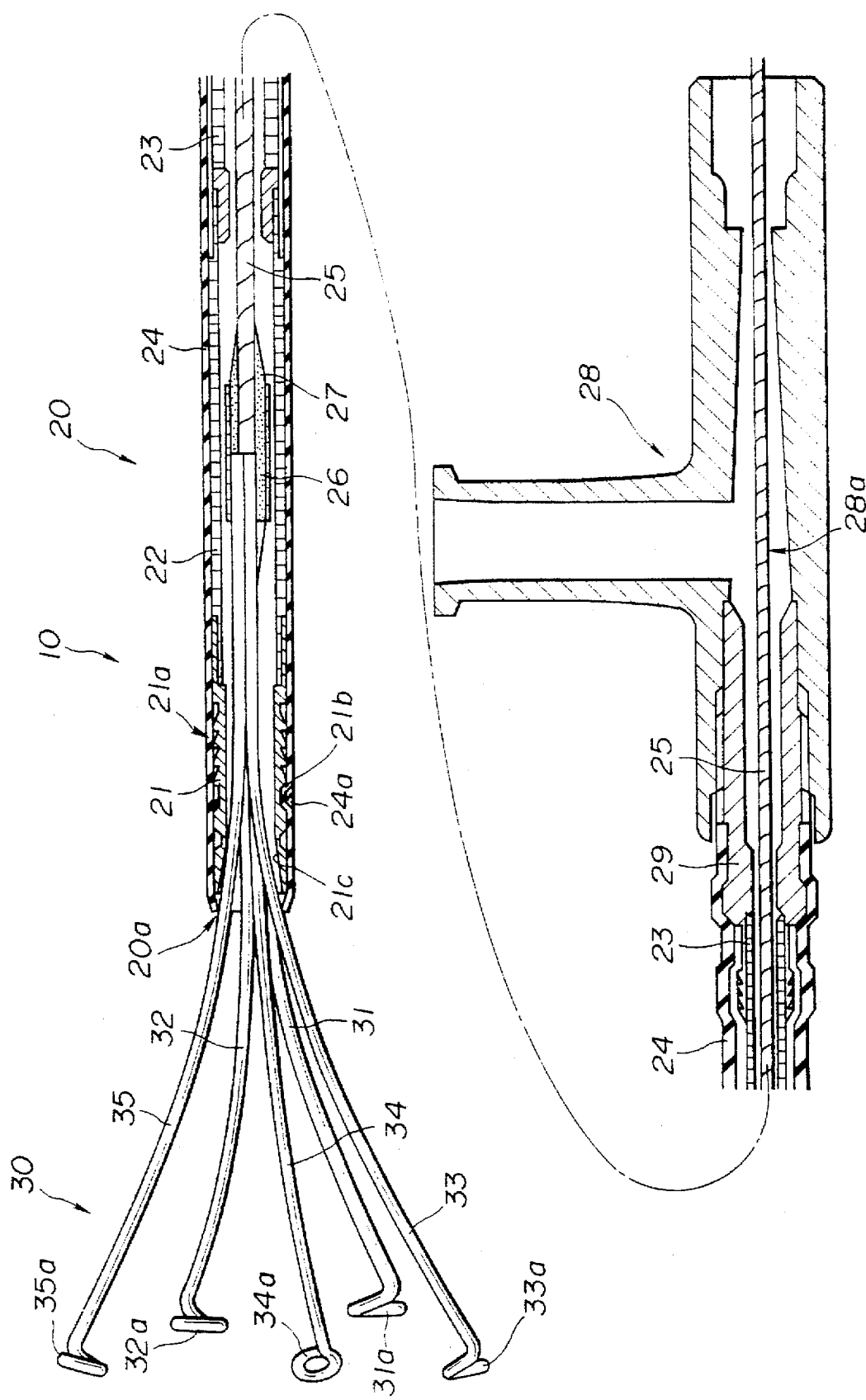

As shown in FIG. 4, the insertion section 20 of the grasping forceps for the endoscope comprises a metallic tubular leading end member 21, a flexible coil sheath 22 on the leading end side and a coil sheath 23 on the base end side which are connected with one another, and the leading end member 21, the coil sheath 22 on the leading end side and the coil sheath 23 on the base end side are externally covered with a flexible integument tube 24. The integument tube 24 serves to prevent turning over at an insertion section leading end face 20a and has a leading end portion of which diameter is smaller than that of the metallic tubular leading end member 21 connected with the leading end of the coil sheath 22 on the leading end side and which projects about 0.5 mm beyond the leading end member 21 so as to prevent exposure of the leading end member 21.

Incidentally, the outer peripheral surface of the leading end member 21 is provided on its proximal side with a plurality of saw-teeth like grooves 21a, 21a . . . for preventing the positional shifting of the integument tube 24 and on the leading end side with integument tube anchoring grooves 21b which are located in front of those plural saw-teeth like grooves 21a, 21a . . . and deeper than the saw-teeth like groove 21a. An anchoring portion 24a between the integument tube 24 and the leading end member 21 is formed by tightly winding a twisted string around the outer periphery of the integument tube 24 located above the integument tube anchoring groove 21b so that the integument tube anchoring grooves catch the integument tube 24 therein and then fixing the twisted string with adhesive. Thereby, an outer diameter of the anchoring portion 24a becomes substantially equal to that of the integument tube 24, so that they can move smoothly from the treating instrument insertion opening 12 formed in the endoscope 11 to the forceps channel (not illustrated) formed within the endoscope insertion section 13. A sheath connection member 29 is connected with adhesive to the hand-end side end portion of the base end side coil sheath 23 constructing the insertion section 20, and this sheath connection member 29 is connected with a cock 28 through threads and adhesive.

The leading end of the operating wire 25 has five elastic grasping members 31, 32, 33, 34, 35 constructing the elastic grasping portion 30 in this embodiment connected to it, and the operating wire 25 passes through the interior of the insertion section 20.

The elastic grasping members 31, 32, 33, 34, 35 are fixedly connected with the operating wire 25 through a coupling tube 26. That is, the hand-end side end portions of the elastic grasping members 31, 32, 33, 34, 35 are bundled and inserted into the coupling tube 26 from one end side and the leading end portion of the operating wire 25 is inserted into the coupling tube 26 from the other end side. The bundled hand-end side end portions of the elastic grasping members 31, 32, 33, 34, 35 and the leading end portion of the operating wire 25 are brought into contact with one another nearly at the middle of the coupling tube 26 and are fixedly connected by soldering so that a hardened portion 27 formed by the soldering is small.

Figure 5A:
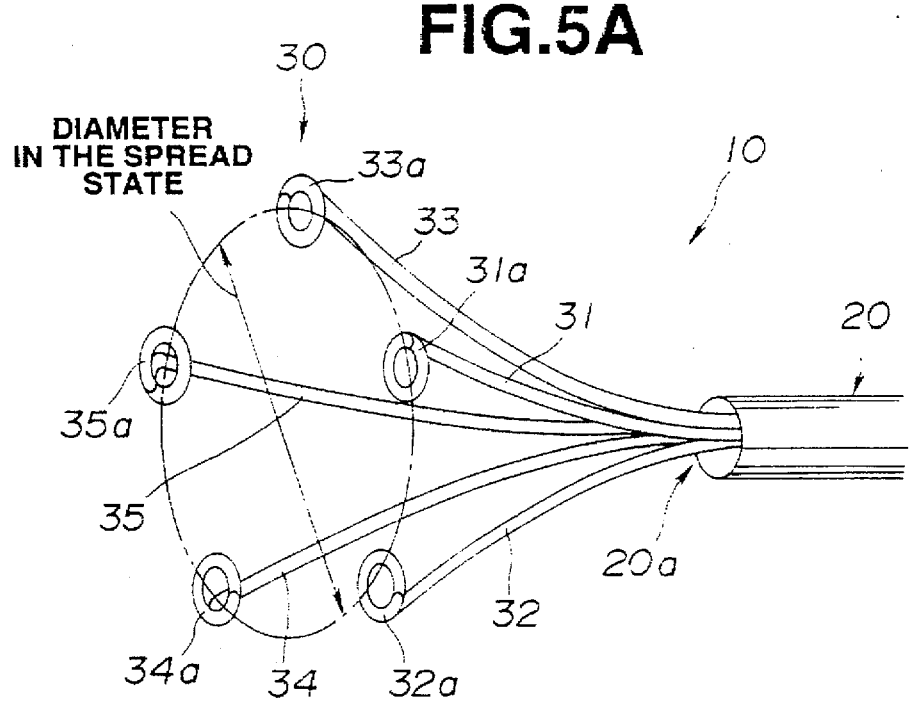
FIGS. 5A and 5B show an opened state of the elastic grasping section of the grasping forceps for the endoscope of the present invention where.
Figure 5B:
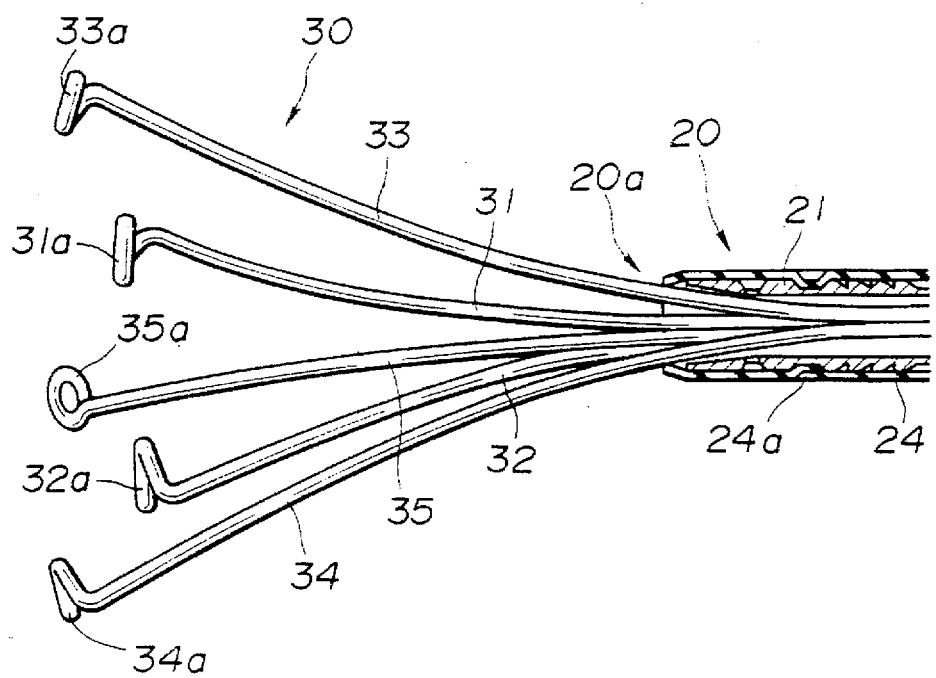

The lengths of the elastic grasping members 31, 32, 33, 34, 35 are different from one another, namely the elastic grasping members are designated by the symbols 31, 32, 33, 34, 35 in the order from the shortest to the longest. As shown in FIGS. 5A and 5B, when circular grasping portions 31a, 32a, 33a, 34a, 35a of the elastic grasping portion 30 composed of the elastic grasping members 31, 32, 33, 34, 35 of different lengths are arranged nearly along an identical circumference in the opened state, and between the shortest elastic grasping member 31 and the longest elastic grasping member 35 there are provided other elastic grasping members such that the longest one 35 and the shortest one 31 are not located adjacent to one another. As shown in FIG. 6, when all the elastic grasping members 31, 32, 33, 34, 35 constructing the elastic grasping section 30 are accommodated within the coil sheath on the leading end side, the respective circular pawl portions 31a, 32a, 33a, 34a, 35a are converged within the insertion section 20 in a longitudinally aligned manner without any superposition.

The circular pawl portions 31a, 32a, 33a, 34a, 35a are formed as the leading end grasping portions at the leading end portions of the elastic grasping members 31, 32, 33, 34, 35, respectively, so as to face inwardly smoothly with respect to the advancing and retreating direction of the operating wire 25 by bending those leading end portions inwardly so as to have nearly 1.3~1.5-fold circularly spiralled configurations. Thereupon, in order to ensure safety, bent portions of the elastic grasping members 31, 32, 33, 34, 35 and bent portions formed at the leading end faces are finished so smoothly that those circular pawl portions 31a, 32a, 33a, 34a, 35a do not cause damage to the body cavity wall. In addition, the bent leading end faces are opposed to the bent portions to prevent rough operation.

Incidentally, a stainless steel wire, a spring stainless steel wire or the like is used for those elastic grasping members 31, 32, 33, 34, 35. Elastic grasping members 31, 32, 33, 34, 35 have a wire diameter of about 0.32 mm so as to permit a great amount of flexing and deflection. The elastic grasping members 31, 32, 33, 34, 35 have a tendency of spreading outwardly from the center axis of the insertion section 20 when they project from the insertion section leading end face 20a thereby forming a circle having a diameter of at least 20 mm in the spread state. This is the reason why the limit for cutting off living body tissue and the like by the endoscope is about 20 mm.

As shown in the above-mentioned FIG. 4, the leading end member 21 is provided in its leading end side inner peripheral surface with an inclined surface portion 21c so that the elastic grasping members 31, 32, 33, 34, 35 can move smoothly.

Further, in order to prevent buckling of the operating wire 25 at the cock 28 having a wide interior space 28a, the surface of the operating wire 25 is coated with wax and the like for improving its sliding capability.

The operating wire 25 is connected at its hand-end side end portion with the finger engagement member 41 of the operating section 40 provided on an operator hand side so as to be operationally pushed and pulled through the interiors of the coil sheath 22 on the leading end side and the coil sheath 23 on the base end side.

Functions of the grasping forceps 10 for the endoscope having the above-mentioned construction will be explained hereinafter.

Firstly, the insertion portion 20 of the grasping forceps 10 for the endoscope is inserted from the treating instrument insertion opening 12 of the endoscope 11 into the treating instrument passing channel thereof under such a condition that the operating wire 25 of the grasping forceps 10 for the endoscope is pulled, namely under such a condition that the circular pawl portions 31a, 32a, 33a, 34a, 35a located at the leading end portions of the elastic grasping section 30 are closed, and then the insertion section 20 is projected from the leading end portion of the endoscope which is inserted near the cellular tissue to be inspected.

When the finger engagement member 41 provided in the operating section 40 of the grasping forceps 10 for the endoscope is pushed so as to move the operating wire 25 toward the leading end side, the elastic grasping members 31, 32, 33, 34, 35 staying within the leading end member 21 and the coil sheath 22 on the leading end side disposed on the insertion section leading end side of the grasping forceps 10 for the endoscope are pushed out of the section portion leading end face 20a. Thereupon, the circular pawl portions 31a, 32a, 33a, 34a, 35a formed at the leading end portions of the elastic grasping members 31, 32, 33, 34, 35 respectively spread outwardly from the central position of the insertion section 20 as a result of the elastic restoring forces of the respective elastic grasping members 31, 32, 33, 34, 35 so as to be arranged along the circle having a diameter of at least 20 mm in the spread state.

Subsequently, the finger engagement member 41 of the operating section 40 is pulled so as to move the operating wire 25 toward the hand-end side. Thereupon, as the elastic grasping members 31, 32, 33, 34, 35 are accommodated into the leading end member 21 and the coil sheath 22 on the leading end side of the insertion section 20, the circular pawl portions 31a, 32a, 33a, 34a, 35a are closed gradually so as to align themselves with the insertion section 20 and to grasp polypus and the like by convergence.

Then the grasping forceps 10 for the endoscope is pulled out of the treating instrument passing channel of the endoscope 11 with the elastic grasping section 30 kept in the closed state to complete the recovery of polypus.

In that way, because the elastic grasping section is composed of at least four elastic grasping members of different lengths as well as the longest elastic grasping member and the shortest elastic grasping member are arranged so as not to be adjacent to each other, the length difference between the adjacent elastic grasping members is decreased. In addition, because the leading end grasping porions of the elastic grasping section composed of the elastic grasping members of different lengths are arranged nearly along the identical circumference, small polypus and the like within a body cavity can be reliably grasped and recovered.

Further, because the leading end portion of the integument tube has a smaller diameter than an outer diameter of the tube and projects about 0.5 mm, the turning over of the integument tube can be prevented. In addition, the inserting and removing thereof relative to the treating instrument passing channel of the endoscope can be carried out smoothly. Because the metallic tubular leading end member connected with leading end portion of the coil sheath on the leading end side is never exposed, safety is increased.

Incidentally, although the elastic grasping portions formed at the leading end portions of the elastic grasping members are the circular pawl portions in the above-mentioned first embodiment, the leading end grasping portions are not limited to the circular pawl portions but may be bent pawl portions formed by bending the leading end portions of the elastic grasping members.

FIG. 7 is a sectional view showing a schematic construction of an insertion section leading end portion of a grasping forceps for an endoscope according to a second embodiment of the present invention.

As illustrated, a grasping forceps 10a for an endoscope of this embodiment has an elastic grasping portion 30a composed of a plurality of elastic grasping members (preferably, only three members are illustrated for simplification) 31, 32, 33 and a needle 36 for recovering polypus and the like by piercing. These plural elastic grasping members 31, 32, 33 and the needle 36 are bundled by a coupling tube 26 and fixedly secured integrally. When the elastic grasping section 30a is brought into the closed state by the traction of the operating wire 25 toward the hand-end side, the needle 36 integrally formed with the elastic grasping portion 30a is set to such a length as to be completely accommodated within the insertion portion. Other constructions are the same as those in the first embodiment, and the same members are designated by the same symbols.

As noted above, since the polypus can be pierced with the needle 36 for recovery by providing for the grasping forceps 10a for the endoscope having the elastic grasping section 30a provided with the needle 36, it becomes possible to recover the plural polypi while the grasping forceps 10a for the endoscope is once inserted into the body cavity through the treating instrument passing channel of the endoscope.

Figure 8:
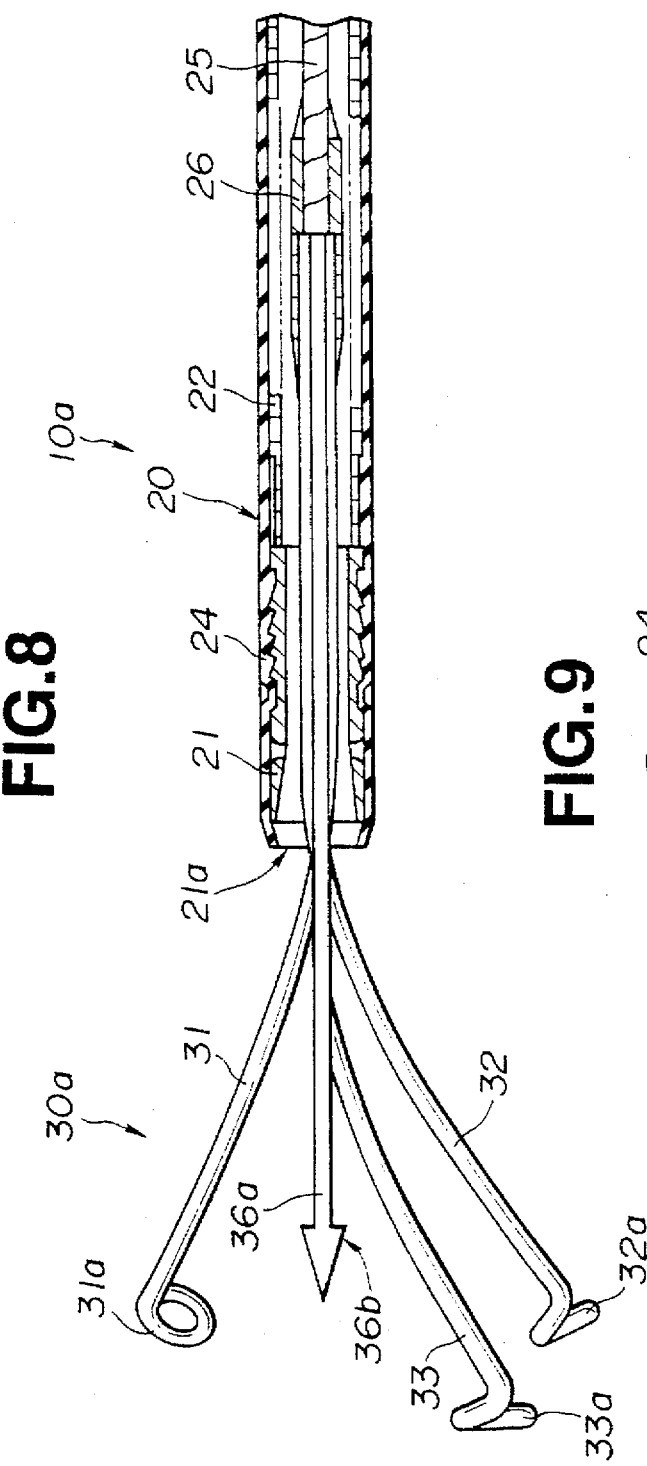
FIG. 8 is a sectional view showing a schematic construction of a leading end portion of an insertion section of a grasping forceps for an endoscope according to a variant example of the second embodiment of the present invention.

Incidentally, the needle 36 mounted to the elastic grasping section 30a of the grasping forceps 10a for the endoscope is not limited to one having a smoothly sharp-pointed leading end, as shown in FIG. 7, but may be one having a step 36b formed at the leading end portion of the needle 36a, as shown in FIG. 8.

When the needle having the step formed at its leading end portion in that way is employed, it becomes possible to recover the plural polypi reliable and readily.

By the way, besides the above-mentioned grasping forceps for the endoscope, a high-frequency snare utilizing high-frequency current and the like may be used as the treating instrument for the endoscope to be inserted into the treating instrument passing channel formed in the endoscope. This high-frequency snare is provided with various kinds of snare wires of the ellipse type, the half-moon type or the mini-ellipse type corresponding to shape and size of the polypus.

Figure 9:
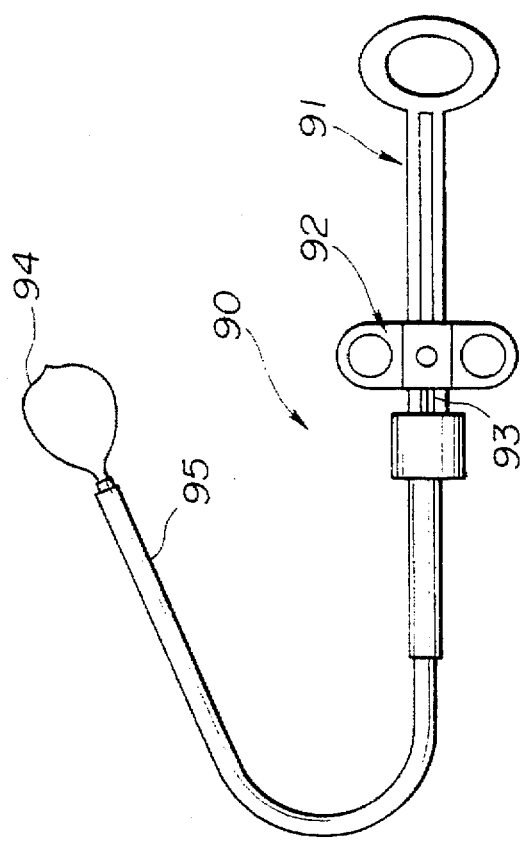
FIG. 9 is an explanatory view showing a schematic construction of a high-frequency snare as another treating instrument for the endoscope passing through an insertion channel thereof for use.

As shown in FIG. 9, generally in a high-frequency snare 90, when a slider 92 disposed in an operating section main body 91 is operationally advanced and retreated, an operating wire 93 connected with the slider 92 is advanced and retreated so that a snare wire 94 connected with the leading end of the operating wire 93 and having a mid portion foldably bent so as to form a loop can be projected and concealed from an insertion portion 95.

That is, whenever the operating wire 93 is pulled toward the hand-end side, the snare wire 94 is accommodated within the insertion portion. When the operating wire 93 is operationally pushed toward the leading end side, the snare wire 94 is projected from the insertion section 95 to spread like a loop as illustrated. Then, the snare wire 94 spread like the loop is made to engage with the polypus, and when the slider 92 of the operating section 91 is operationally pulled toward the hand-end side, the polypus is strongly tightened by the snare wire 94. Subsequently, when high-frequency current is supplied to the snare wire 94 through the operating wire 93, the polypus strongly tightened by the snare wire 94 is cut off by heat.

Figure 10A:
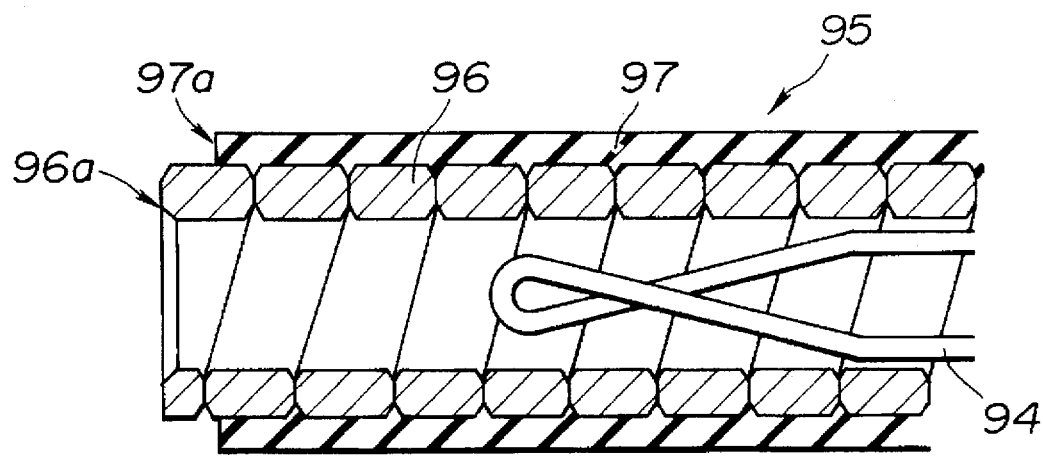
FIG. 10A is a sectional view showing a construction of a leading end portion of an insertion section of a conventional high-frequency snare.

But, as shown in FIG. 10A, the insertion section 95 of this high frequency snare 90 has a coil sheath 96 covered with an integument tube 97 formed by a flexible insulating synthetic resin such that the leading end face 97a of this integument tube 97 coincides with the leading end face 96a of the coil sheath 96 or takes a hand-end side position behind the coil sheath leading end face 96a. Thereby, while the high-frequency snare 90 is repeatedly inserted into and drawn out of the treating instrument passing channel (not illustrated) of the endoscope, the leading end face 97a of the integument tube 97 is turned over to expose the coil sheath 96. Therefore, an increased force is required for inserting and drawing the high-frequency snare 90 into and out of the treating instrument passing channel and the exposed coil sheath 96 might contact a mucosa at a location other than at a desired location within a body cavity, or the exposed coil sheath 96 in contact with the snare wire 94 may burn the touched location at the time of supplying high-frequency current.

Figure 10B:
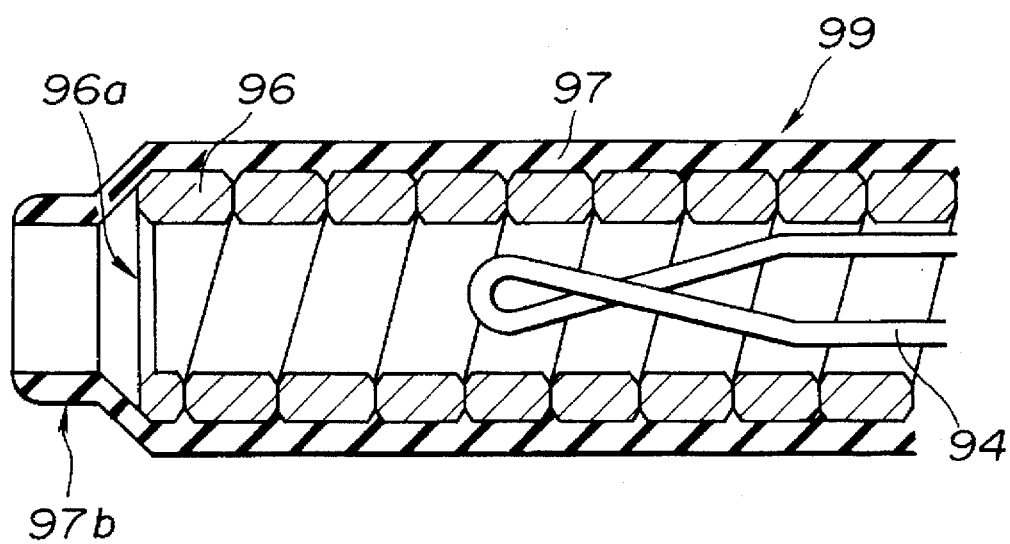
FIG. 10B is a sectional view showing a leading end portion of an insertion section of a high-frequency snare applied with the construction of the leading end portion of the insertion section of the grasping forceps for the endoscope according to the present invention.

Thereupon, the insertion section of the high-frequency snare 90 is constructed as shown in FIG. 10B, in which by operationally advancing and retreating the slider 92 disposed in the operating section main body 92, as shown in FIG. 9, the operating wire 93 connected with the slider 92 is advanced and retreated so as to project and conceal the snare wire 94 disposed at the leading end portion of the operating wire 93 from the insertion section 95.

That is, the insertion section 99 of the high-frequency snare 90 is composed of the flexible coil sheath 96 and the integument tube 97 formed from thermo-plastic synthetic resin, for example, such as flexible insulating ethylene tetrafluoride resin and polyethylene, and the coil sheath 96 is covered with the integument tube 97 which projects from the leading end face 96a of the coil sheath 96.

That is, the insertion section 99 is constructed by covering the coil sheath 96 with the integument tube 97. Thereupon, a projecting portion 97b having a diameter smaller than the outer diameter of the integument tube 97 and projecting about 0.5 mm from the leading end face of the coil sheath 96 is formed at the leading end portion of the integument tube 97.

Functions of the high-frequency snare 90 having the above-mentioned construction will be explained hereinafter.

Firstly, the high-frequency snare 90 is inserted into a body cavity through the treating instrument passing channel formed in the endoscope under such a condition that the operating wire 93 is pulled toward the hand-end side, namely under such a condition that the snare wire 94 is accommodated within the insertion portion. Then, the insertion section leading end portion is made to closely approach the aimed location under observation by the endoscope.

Next, the snare wire 94 is made to project from the insertion section and spread by pushing the operating wire 93 toward the leading end side. Then, the spread snare wire 94 is engaged with the polypus and the like and strongly tightens the polypus by operationally pulling the operating wire 93 toward the hand-end side, and high-frequency current is supplied to the snare wire 94 through the operating wire 93 to thermally cut off the polypus tightened strongly by the snare wire 94.

In this way, when the insertion section of the high-frequency snare is constructed by covering the coil sheath with the integument tube, the integument tube covering the coil sheath is made to project from the leading end face of the coil sheath so as to have the projecting portion of a smaller diameter than the coil sheath. Therefore, the turning over of the integument tube can be prevented, so that the insertion and draw within the treating instrument passing channel of the endoscope can be performed smoothly. Thus, because the exposing of the coil sheath which might be caused by the turning over of the integument tube can be prevented, the coil sheath does not touch the mucosa of the body cavity at a location other than at the desired location.

It will be apparent that various different embodiments can be constructed based on the present invention without departing from the spirit and scope of the invention. Accordingly, it is not intended that the present invention is limited by the specific embodiments, except as by the appended claims.

What is claimed is:

1. A grasping forceps for an endoscope including:
   a flexible insertion section;
   an operating wire adapted to pass through said insertion section and to be advanced and retreated in accordance with the operation of an operating section connected with a proximal side end portion thereof; and
   at least four elastic grasping members having different lengths arranged at a leading end portion of said operating wire and being flexible such that leading end grasping portions formed at their leading end portions respectively spread outwardly from a central position of said insertion section;
   wherein said at least four elastic grasping members are sequentially arranged in the order of increasing length to said leading end grasping portions with respect to a leading end face of said insertion section, and wherein other elastic grasping members are provided between and contiguous to both the longest elastic grasping member and the shortest elastic grasping member to said leading end grasping portions in the circularly spread state of said elastic grasping members.

2. A grasping forceps for an endoscope as recited in claim 1, wherein one of a stainless steel wire and a spring stainless steel wire is used for each of said elastic grasping members.

3. A grasping forceps for an endoscope as recited in claim 1, wherein a diameter of a circle formed by the circularly spread state of said elastic grasping section is at least 20 mm.

4. A grasping forceps for an endoscope as recited in claim 1, wherein said elastic grasping section comprises five elastic grasping members, and a wire diameter of each elastic grasping member is about 0.32 mm.

5. A grasping forceps for an endoscope as recited in claim 1, further comprising an integument tube consisting of flexible synthetic resin forming an outermost peripheral surface of said flexible insertion section, wherein a leading end portion of said integument tube has a smaller diameter than the outer diameter of the rest of said integument tube.

6. A grasping forceps for an endoscope as recited in claim 5, wherein the leading end portion of said integument tube projects at least 0.5 mm from a leading end face of a member externally covered by said integument tube.

7. A grasping forceps for an endoscope as recited in claim 5, wherein said synthetic resin forming said integument tube consists of thermo-plastic resin such as tetrafluoroethylene resin and polyethylene.

* * * * *